United States Patent [19]

Smith

[11] Patent Number: 5,443,469
[45] Date of Patent: Aug. 22, 1995

[54] INTRAMEDULLARY REAMING TISSUE PROTECTION GUARD

[76] Inventor: Aubrey L. Smith, 13 Medical Dr., Amarillo, Tex. 79106

[21] Appl. No.: 236,197

[22] Filed: May 2, 1994

[51] Int. Cl.$^6$ ............................................. A61F 5/00
[52] U.S. Cl. ................................... 606/86; 606/96
[58] Field of Search .............................. 606/62–68, 606/80, 85, 86, 87, 88, 96, 97, 98, 99, 102; 623/16–23

[56] References Cited

U.S. PATENT DOCUMENTS

| | | | |
|---|---|---|---|
| 4,312,337 | 1/1982 | Donohue | 606/80 |
| 4,541,424 | 9/1985 | Grosse | 606/98 |
| 4,678,471 | 7/1987 | Noble | 606/62 |
| 4,781,181 | 11/1988 | Tanguy | 606/80 |
| 4,844,064 | 7/1989 | Thimsen | 606/80 |
| 4,941,466 | 7/1990 | Romano | 606/80 |
| 4,985,032 | 1/1991 | Goble | 606/96 |
| 5,052,411 | 10/1991 | Schoolman | 606/80 |
| 5,312,408 | 5/1994 | Brown | 606/80 |

*Primary Examiner*—Michael A. Brown
*Attorney, Agent, or Firm*—Harold H. Flanders

[57] ABSTRACT

An intramedullary reaming tissue protection guard consisting of a cylindrical tube and having means of applying suction is disclosed.

3 Claims, 2 Drawing Sheets

INTRAMEDULLARY REAMING TISSUE PROTECTION GUARD

FIELD OF THE INVENTION

In general, the present invention relates to a surgical device. In particular, the present invention is an intramedullary reaming tissue protection guard.

BACKGROUND OF THE INVENTION

While there are many, various retractor devices which have been and are employed, most suffer from the fact that they are not specifically designed or adapted to reaming operations.

The present invention overcomes the deficiencies of the prior art as described above by means of a special tubular device, which taken as a whole constitutes a new and novel intramedullary reaming tissue protection guard.

SUMMARY OF THE INVENTION

Accordingly, it is an object of the present invention to provide a new, and highly effective design and method which overcomes the deficiencies of the prior art as described above.

It is a further object of the present invention to provide an intramedullary reaming tissue protection guard.

Other objects and a fuller understanding of the invention may be had by referring to the following description and claims taken in conjunction with the accompanying drawings.

The present invention overcomes the deficiencies of the prior art and achieves its objectives by providing a new, novel design and method of achieving the protection of sensitive tissue during intramedullary reaming operations. The present invention consists of a cylindrical, tubular member which when properly placed acts as a retractor for and a protector of adjacent tissue during intramedullary reaming operations.

BRIEF DESCRIPTION OF THE DRAWINGS

In order to facilitate the understanding of the present invention, reference will now be made to the appended drawings of a preferred embodiment of the present invention. The drawings should not be construed as limiting the invention, but rather as being exemplary only.

DESCRIPTION OF THE INVENTION

The following is a description of a preferred embodiment of the present invention. The general design of the present invention may be appreciated by reference to the drawings. As will be noted in greater detail hereinafter, the details of the geometries employed may be varied widely to meet specific situations and requirements. However, for purposes illustration, cylindrical configurations and other common surfaces of revolution are here employed.

As shown in the Figures, the tissue protection reaming guard of the present invention is basically a cylindrical tube which is intended to protect the sensitive soft tissues during the process of reaming the intramedullary canals of long bones. The reaming of long bones is needed and is a preparatory phase for the actual insertion of an intramedullary nail holding the long bone together and in proper alignment. During this process a flexible reamer is placed over a long guide wire running down the intramedullary canal of a long bone, such as the femur. The flexible reamer is progressively inserted and then retracted out of the long bone while running to produce a reaming of the intramedullary canal to a consistent diameter. This procedure requires that the soft tissue be protected and held away from the moving, flexible reaming apparatus. It is the intent of the present invention to provide a reaming guard to protect the soft tissues during this particular part of such procedures.

Figure 2:
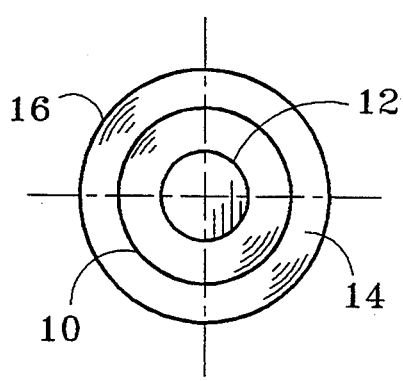
FIG. 2 is a top view of the guard of FIG. 1.
Figure 4:
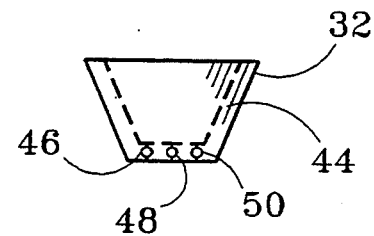
FIGS. 4, 5, 6, and 7 are alternative means of facilitating suction.

As noted above the device of the present invention may consist of a cylindrical tube 10 which may at its leading end be tapered in a truncated conic section 12 to facilitate it insertion into the incision or wound. As used herein the term leading end refers to the end of the device inserted into the incision or wound and may be considered to be the proximate end to the bone being reamed. The tube 10 may also be tapered in a transitional section 14 which may also be a truncated conic section to a remote end section 16 which is intended to be sufficiently large in diameter to permit easy insertion of the reaming apparatus and its easy movement and adjustment. The respective transitional sections noted above are shown in FIG. 2. A slot 15 is provided in one side of the tube 10 of sufficient with to accommodate the reamer being repeatedly inserted and withdrawn.

The device of the present invention may, also, consist of a cylindrical tube 30 which may at its leading end be tapered in a truncated conic section 32 to facilitate it insertion into the incision or wound. The tube 10 may also be tapered in a transitional section 34 which may also be a truncated conic section to a remote end section 36 which is intended to be sufficiently large in diameter to permit easy insertion of the reaming apparatus and its easy movement and adjustment. Within the tube 30 a suction tube 42 may be provided as an integral part of the wall of tube 30 ending in a nipple 40 for attachment of tubing from a conventional suction device(not shown). The suction tube 42 may end in a double walled section 44 in tapered section 32 to facilitate the suctioning and removal of fluids and debris.

Again it should be noted that a slot 35 may be provided in the side of tube 30 to accommodate the insertion and withdrawal of the reamer by the surgeon.

Figure 1:
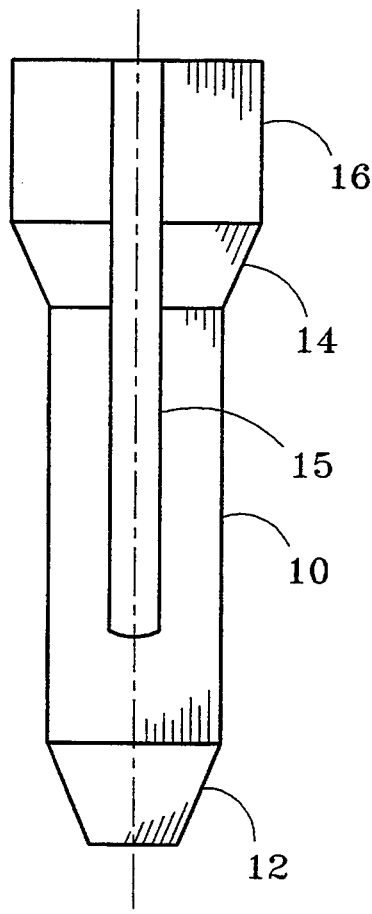
FIG. 1 is a side view of the tissue protection, reaming guard.
Figure 3:
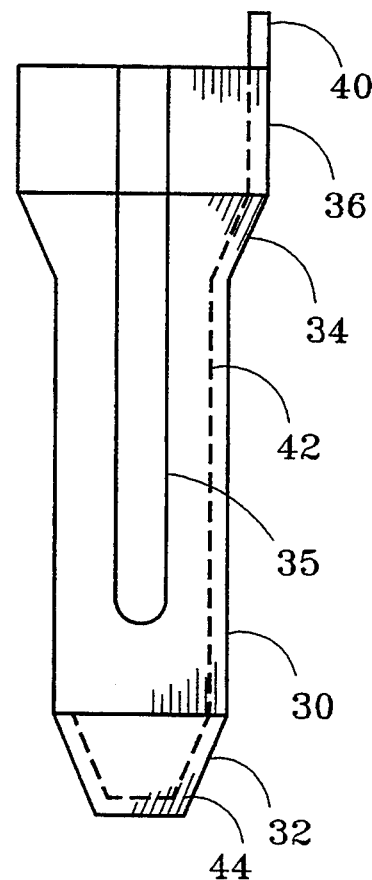
FIG. 3 is a side view of the guard of the present invention showing means for the provision of suction.

The provision of the capability of providing suctioning within the incision or wound as well as protection of the adjacent soft tissue is an important contribution and part of the present invention. By means of the double wall section 44 as shown in FIG. 3, or by means of a series of holes 46, 48, and 50 within the wall section 32, suctioning forces may be applied within the wound when the device is inserted into the wound. By attachment to a vacuum hose intra-operatively the reamings of the intramedullary canal can be collected into the holes 46, 48, 50 and/or the double walled section 44 and removed from the wound.

This feature of the present invention is an important characteristic and provides an important capability that is most useful in the reaming of long bones by providing a clearance of the intramedullary contents out of the wound. It is notable that bone and bone fragments of the intramedullary canal that remain within the wound at the end of the surgery may lead to extra bone formation later on providing protuberant or painful areas of ossification in muscle tissue. The better collection of the intramedullary contents provides an important, additional, helpful technique in the intramedullary nailing process which assists the surgeon in the removal of the intramedullary content to prevent heterotopic bone formation.

Figure 5:
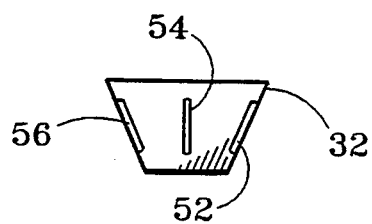
Figure 6:
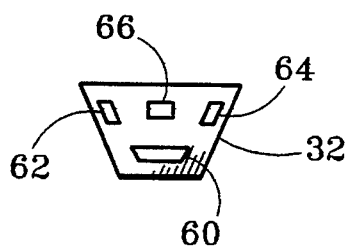

FIG. 5 shows a further alternative in which slots 52, 54, and 56 permit the application of suction within the wound. Similar forces may be applied through slots 60, 62, 64, and 66 as shown in FIG. 6.

Figure 7:
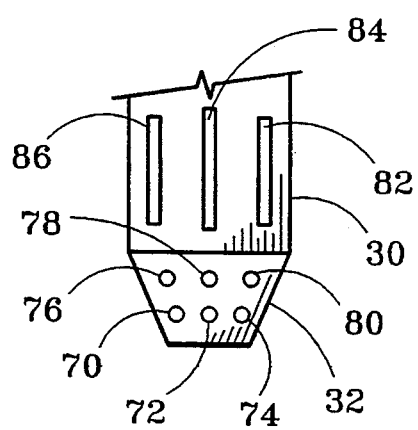

FIG. 7 shows a further alternative embodiment in which suction may be applied not only through holes 70, 72, 74, 76, 78, and 80 of section 32 but also by means of slots 82, 84, and 86 in the side of tube 30.

The device of the present invention may come in a variety of lengths with a diameter adequate to accommodate the reaming apparatus. The diameter may typically be on the order of one inch and the length may typically range between 8 and 16 inches. Portal holes to permit the vacuum extraction and removal of debris may be variably placed around and about the tube.

The shape of the device may be straight or curved. The device may be made sufficiently flexible so that it may be curved and shaped as needed for the particular anatomy at hand.

The necessary flexibility may be obtained by the provision of a ribbed surface which will allow the device to be flexed into different positions and to hold that particular position.

Figure 8:
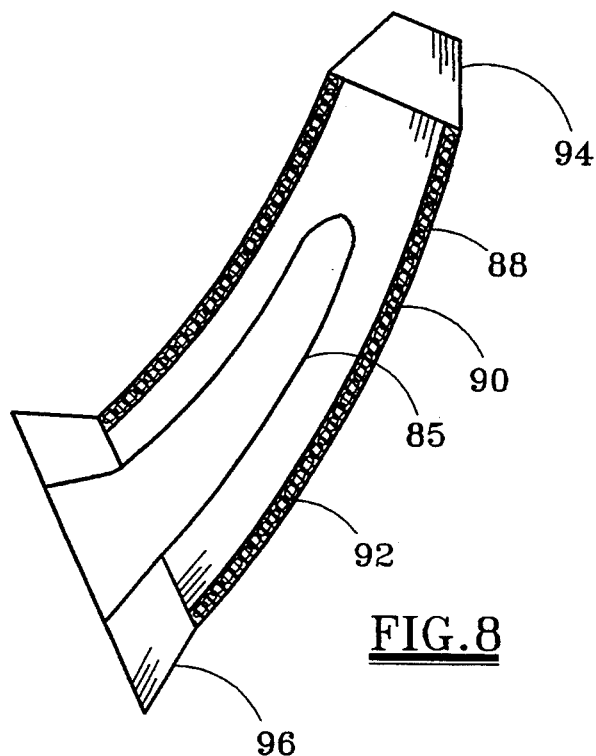
FIG. 8 shows a curved embodiment of the present invention.

A further embodiment is shown in FIG. 8 in which a flexible section 88 is provided between conic sections 96 and 94. Section 88 may be made adjustably flexible by means of flexible chain links 90 embedded within plastic wall 92 to give the wall structure additional rigidity while at the same time permitting the same type of flexibility as provided in similarly structured flexible "French curves". Other shapes or configurations of the tubular device too allow for flexibility may be incorporated in accordance with the present invention. Also, a slot 85 may be provided in the tube on the side toward the surgeon to accommodate the reamer and its necessary insertion and withdrawal.

Thus, the present invention consists of a cylindrical body which protects the soft tissue of an incision or wound from damage in reaming operations.

While specific components such as cylindrical tube shaped devices may be employed and have been referred to throughout as a part of the preferred embodiment of the present invention, any other suitable components or elements which perform the same function, such as hexagonally shaped tubes may be used.

The parts herein described may be made of any suitable plastic material.

The preferred embodiment has been described in terms of standard cylindrical configurations, but other geometric shapes may be employed using the teachings of the present invention.

The present invention has been described in terms of its specific, preferred embodiment but it may obviously be employed in other contexts and operations.

While the present invention has been described with reference to specific embodiments, this application is intended to cover those various changes and substitutions which may be made by those skilled in the art without departing from the spirit and scope of the appended claims.

What is claimed is:

1. An intramedullary reaming, tissue protection guard comprising a cylindrical tube, said tube having a tapered leading end, at least a portion of said tube being double walled and having opening means therein for applying suction at or adjacent to said leading end and said tube having a slot incorporated within it at its other end and in a portion of said tube to accommodate the insertion and withdrawal of the reaming apparatus.

2. The device of claim 1 wherein the guard is flexible.

3. The device of claim 1 wherein the guard is curved.

* * * * *